United States Patent [19]

Mues et al.

[11] Patent Number: 4,568,755

[45] Date of Patent: Feb. 4, 1986

[54] CHLOROCARBONIC ESTERS AND POLYCYCLIC CARBONIC ESTERS OBTAINABLE THEREFROM

[75] Inventors: Peter Mues; Bert Brassat; Hans-Josef Buysch, all of Krefeld, Fed. Rep. of Germany

[73] Assignee: Bayer Aktiengesellschaft, Leverkusen, Fed. Rep. of Germany

[21] Appl. No.: 647,248

[22] Filed: Sep. 4, 1984

[30] Foreign Application Priority Data

Sep. 16, 1983 [DE] Fed. Rep. of Germany ....... 3333413

[51] Int. Cl.$^4$ ................... C07D 321/00; C07D 319/06
[52] U.S. Cl. .................................... 549/228; 528/370; 528/372
[58] Field of Search ......................................... 549/228

[56] References Cited

U.S. PATENT DOCUMENTS 4,440,937  4/1984  Krimm et al. ...................... 549/228
4,501,905  2/1985  Krimm et al. ...................... 549/228

FOREIGN PATENT DOCUMENTS 0057360  8/1982  European Pat. Off. .

Primary Examiner—Harold D. Anderson

Attorney, Agent, or Firm—Sprung, Horn, Kramer & Woods

[57] ABSTRACT

New chlorocarbonic esters of the formula

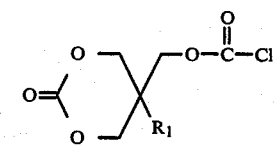

new polycyclic carbonic esters of the formula

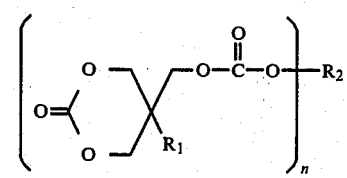

and new copolymers obtainable by copolymerization of the new polycyclic carbonic esters of the formula (III) with monocyclic carbonates.

10 Claims, No Drawings

CHLOROCARBONIC ESTERS AND POLYCYCLIC CARBONIC ESTERS OBTAINABLE THEREFROM

The present invention relates to new chlorocarbonic esters of the formula (I)

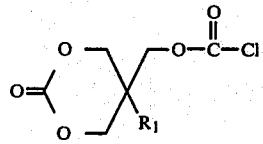

in which $R_1$ represents an alkyl radical having 1 to 4 C atoms. $R_1$ preferably represents a methyl or ethyl group.

The new chlorocarbonic esters of the formula (I) can be prepared by reacting phosgene with the alochols of the formula (II)

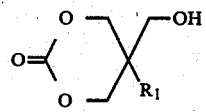

in which $R_1$ has the abovementioned meaning.

The alcohols of the formula (II) can be prepared by the process described in German Offenlengungsschrift No. 3,103,139.

The reaction of phosgene with the alcohols of the formula (II) can be carried out such that, for example, phosgene in a solvent is initially introduced, and the alcohol of the formula (II), together with an acid-binding agent, is gradually added at temperatures in the range from $-5°$ to $+5°$ C. Phosgene is preferably employed in excess in this reaction, for example in 5 to 20% molar excess. Examples of possible solvents are chlorinated hydrocarbons, such as methylene chloride. Examples of suitable acid-binding agents are aromatic or aliphatic amines, such as N,N-dimethylaniline, pyridine or triethylamine. Examples of alcohols of the formula (II) to be used are trimethylolethane carbonate, trimethylopropane carbonate, trimethylolbutane carbonate and trimethylolpentane carbonate.

The new chlorocarbonic esters of the formula (I) can be isolated from the mixture after reaction with phosgene by, for example, removing all readily volatile components from the reaction mixture by vacuum distillation, taking up the residue in a solvent for the chlorocarbonic esters of the formula (I), for example toluene, separating off insoluble constituents, and again removing the solvent.

The present invention also relates to new polycyclic carbonic esters of the formula (III)

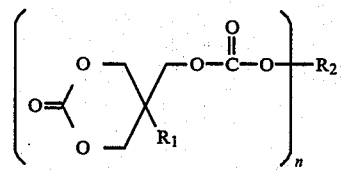

in which
$R_1$ represents an alkyl radical having 1 to 4 C atoms,
$R_2$ represents an alkylidene radical having 3 to 18 C atoms, an arylene radical having 6 to 12 C atoms, or an aralkylene radical having 7 to 24 C atoms, and n denotes 2, 3 or 4.

In formula (III), $R_1$ preferably represents methyl or ethyl, and $R_2$ preferably represents the hydrocarbon skeleton of one of the following dihydric to tetrahydric alcohols: trimethylolethane, trimethylolpropane, pentaerythritol, 1,4-butanediol, 2-butene-1,4-diol, 2-butyne-1,4-diol, neopentylglycol, 1,6-hexanediol, 2-methylene-1,3-propanediol, 1,4-cyclohexanediol, cyclohexane-1,4-dimethanol, bisphenol A and perhydrobisphenol A. In these instances, n corresponds to the number of hydroxyl groups in the alcohol whose skeleton is represented by the radical $R_2$. $R_2$ is particularly preferably the hydrocarbon skeleton of a dihydric or trihydric alcohol, and is very particularly preferably the hydrocarbon skeleton of a dihydric alcohol, that is to say n particularly preferably represents 2 or 3, and very particularly preferably represents 2.

The new polycyclic carbonic esters of the formula (III) can be prepared by, for example, gradually adding chlorocarbonic esters of the formula (I) to a solution which contains a dihydric to tetrahydric alcohol and an acid-binding agent, at temperatures in the range from 0° to 30° C.

It is not absolutely necessary for the preparation of the new polycyclic carbonic esters of the formula (III) that the chlorocarbonic esters of the formula (I) are used in the pure form; for example, they can also be used in the form of the crude solution resulting from their preparation. The dihydric to tetrahydric alcohols are those whose hydrocarbon skeleton is an alkylidene radical having 3 to 18 atoms, an aryl radical having 6 to 12 C atoms or an aralkyl radical having 7 to 24 C atoms. The dihydric to tetrahydric alcohols are preferably an alcohol from the group comprising trimethylolethane, trimethylolpropane, pentaerythritol, 1,4-butanediol, 2-butene-1,4-diol, 2-butyne-1,4-diol, neopentylglycol, 1,6-hexanediol, 2-methylene-1,3-propanediol, 1,4-cyclohexanediol, cyclohexane-1,4-dimethanol, bisphenol A and perhydrobisphenol A. Examples of suitable acid-binding agents are aromatic or aliphatic amines, such as N,N-dimethylaniline, pyridine or triethylamine. Examples of possible solvents are chlorinated hydrocarbons, such as methylene chloride.

The isolation and purification of the new polycyclic carbonic esters of the formula (III) can be carried out by, for example, first extracting the hydrochloride, which has been produced from the acid-binding agent, from the reaction mixture using water or an aqueous salt solution, removing the solvent from the remaining organic phase, where appropriate after drying, and crystallizing from a suitable solvent, for example butyl acetate, the crude product thus obtained.

The present invention also relates to new copolymers which can be obtained by copolymerization of the new polycyclic carbonic esters of the formula (III) with monocyclic carbonates. Examples of monocyclic carbonates which can be used in the copolymerization are those which correspond to the formulae, (IV), (V) or (VI):

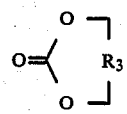

in which $R_3$ represents $-CH_2-_m$, wherein m represents 3, 4, 5 or 6, or $R_3$ represents $-CH_2-CH=CH-CH_2-$, $-CH_2-CH_2-CH(CH_3)-$, $-CH_2-CH_2-O-CH_2-CH_2-O-CH_2-CH_2-$,

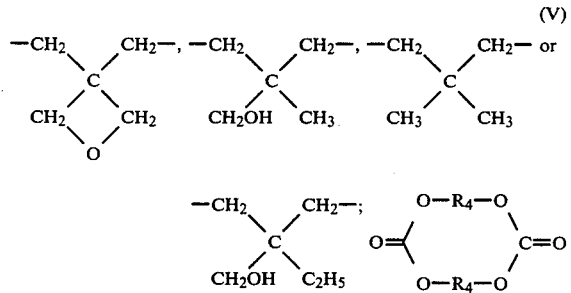

(V)

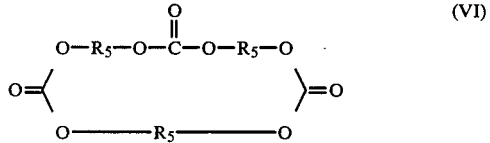

in which $R_4$ represents $-CH_2-_p$, wherein p denotes an integer from 4 to 12, or $R_4$ represents $-CH_2-CH_2-O-CH_2-CH_2-$, $-CH_2-CH_2-O-CH_2-CH_2-O-CH_2-CH_2-$ or (VI)

$$O-R_5-O-\overset{O}{\overset{\|}{C}}-O-R_5-O$$
$$O=\langle\qquad\rangle=O$$
$$O\text{———}R_5\text{———}O$$

in which $R_5$ represents $-CH_2-CH_2-O-CH_2-CH_2-$.

The preparation of monocyclic carbonates of these types is described in, for example, German Offenlegungsschriften Nos. 3,103,135, 3,103,139, (U.S. Pat. No. 4,440,937), 3,103,140 and 3,204,078, (U.S. patent application Ser. No. 460,686).

Monocyclic carbonates of the formula (IV) are preferably employed, particularly preferably 5,5- dimethyl-1,3-dioxan-2-one.

In the copolymerization of the new polycyclic carbonic esters of the formula (III) with the monocyclic carbonates, the ring in the monocyclic carbonates is opened and linear polycarbonates are produced, and these are crosslinked by the structural units originating from the new polycyclic carbonic esters of the formula (III). These copolymers are thermosetting plastics with improved properties, in particular having surprisingly high impact strengths.

For the copolymerization, for example 2 to 50, preferably 5 to 20, % by weight of a polycyclic carbonic ester of the formula (III) and 98 to 50, preferably 95 to 80, % by weight of a monocyclic carbonates are employed (these percentages by weight relate in each case to the total amount of organic carbonates employed). In general, the copolymerization is carried out at elevated temperature, for example at temperatures in the range from 80° to 200° C. Temperatures in the range from 100° to 160° C. are preferred. Temperatures in the range from 110° to 140° C. are particularly preferred. Moreover, the copolymerization is generally carried out with the addition of catalysts. Examples of suitable catalysts are the carbonates and carboxylates of the metals lithium, sodium, potassium, tin, lead and thallium. Carboxylates of lithium, lead and thallium are preferred. The catalysts can be employed in, for example, amounts of from 0.01 to 0.1% by weight relative to the total amount of carbonates employed. Amounts of catalysts of from 0.01 to 0.05% by weight are preferred.

The thermosetting plastics which can be obtained by this copolymerization can be advantageously employed in every instance where there are stringent requirements for the properties typical of thermosetting plastics, such as heat distortion resistance and insensitivity to agents which may induce dissolution or swelling (for example fuels and lubricants), and where, in addition, good mechanical properties, in particular great toughness, are necessary. For example, it is possible to manufacture parts of motor vehicles from thermosetting plastics of these types, in particular those which are exposed to the danger of impact by stones, such as spoilers, bumpers (and parts) and mudguards (and coatings).

The examples which follow illustrate the invention without restricting it in any manner.

EXAMPLES

Example 1

A solution of 80 g (0.5 mol) of 5-hydroxymethyl-5-ethyl-1,3-dioxan-2-one and 39.5 g (0.5 mol) of pyridine in 200 ml of dried methylene chloride was added dropwise, within 40 min., to a solution of 53 g (0.535 mol) of phosgene in 200 ml of dried methylene chloride at 5° C. The mixture was stirred at 0° C. for a further 3 hours. Then 100 ml of methylene chloride was distilled out under waterpump vacuum. The portion of pyridine hydrochloride which precipitated out was filtered off with suction and washed with a little methylene chloride. The filtrate was concentrated at 0° C. using a rotary evaporator. The crystalline residue (163 g) was stirred 3 times with a total of 1.6 l of toluene, and the insoluble constituents were filtered off with suction. The filtrate was concentrated at 30° C. using a rotary evaporator. 79 g (71% of theory) of crystalline product with a melting point of 62° to 65° C. remained.

The $^1$H NMR spectrum and the analytical determination of chlorine confirmed the structure and composition of the resulting product as being a compound of the formula (I) with $R_1=C_2H_5$.

Example 2

160 g (1 mol) of 5-hydroxymethyl-5-ethyl-1,3-dioxan:2-one dissolved in 95 g (1.2 mol) of pyridine and 700 ml of dried methylene chloride was added dropwise, within 2 hours, to a solution of 110 g (1.1 mol) of phosgene in 400 ml of dried methylene chloride at 4° C. After a further 2 hours, the resulting solution was added, within 25 min., to a mixture of 82 g (0.75 mol) of cyclohexane-1,4-dimethanol, 79 g (1 mol) of pyridine and 200 ml of methylene chloride at 20° C. After 15 hours at room temperature, the mixture was extracted 3 times with a total of 1 l of saturated aqueous NaCl solution. The organic phase was dried over $Na_2SO_4$ and evaporated under mild conditions (bath temperature 40° C.) using a rotary evaporator. Residual solvent was removed under oil pump vacuum. The crude product (286 g) was dissolved in 900 ml of hot butyl acetate. On cooling to room temperature, and later of 5° C, 155 g of product precipitated out (60% of theory relative to 5-hydroxymethyl-5-ethyl-1,3-dioxan-2-one, with a melting point of 95°–102° C.)

The $^1$H NMR spectrum confirmed the structure and composition of the resulting product as being a compound of the formula (III) with $R_1=C_2H_5$, $R_2=$

and n=2.

Example 3

The process was carried out as in Example 2, but the cyclohexane-1,4-dimethanol was replaced by the corresponding amount of 2,2-dimethyl-1,3-propanediol (=neopentyl glycol). A product with a melting point of 74° C. was obtained. The $^1$H NMR spectrum confirmed the structure of the resulting product as being a compound of the formula (III) with $R_1=C_2H_5$, $R_2=$

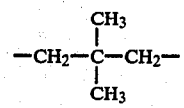

and n=2.

Example 4

The process was carried out as in Example 2, but the cyclohexane-1,4-dimethanol was replaced by the corresponding amount of perhydrobisphenol A. A product with a melting point of 190° to 200° C. was obtained. The $^1$H NMR spectrum confirmed the structure of the resulting product as being a compound of the formula (III) with $R_1=C_2H_5$, $R_2=$

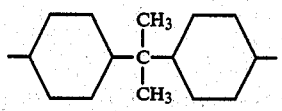

and n=2.

Example 5

The process was carried out as in Example 2, but the cyclohexane-1,4-dimethanol was replaced by the corresponding amount of bisphenol A. A product with a melting point of 132°–135° C. was obtained. The $^1$H NMR spectrum confirmed the structure of the resulting product as being a compound of the formula (III) with $R_1=C_2H_5$, $R_2=$

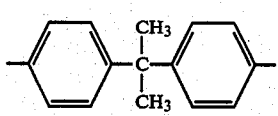

and n=2.

Example 6
153 g (1.18 mol) of 5,5-dimethyl-1,3-dioxan-2-one (formula (IV), $R_3=$

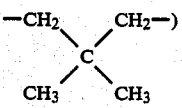

and 17 g (0,033 mol) of 5,5'-(cyclohexyl-1,4-bis(methyleneoxy-carboxy(oxymethylene)) bis (5-ethyl-1,3-dioxane-2-one (formula (III), $R_1=C_2H_5$, $R_2=$

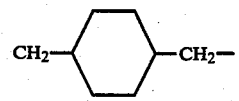

and n=2) were fused at 120° C. After addition of 17 mg of thallium acetate, the mixture was heated to 125° C. After 20 minutes, polymerization started and gave an infusible transparent polymer which was insoluble in solvents and had great toughness, hardness, and elasticity. The polymer was heat-treated at 125° C. for a further 30 minutes.

Example 7

The properties of the product from Example 6 and, in comparison with this, those of a product which was prepared according to the state of the art (German Offenlegungsschrift No. 3,103,139) from 90% by weight of 5,5-dimethyl-1,3-dioxan-2-one and 10% by weight of the carbonate of the formula

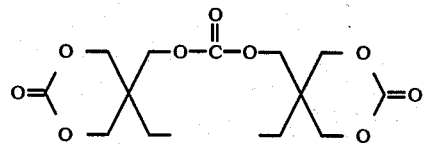

were determined. The results can be seen in Table 1.

TABLE 1

|  |  | State of the art | Product from Example 6 |
|---|---|---|---|
| Tensile strength | R (MPa) | 26 | 30 |
| Elongation at break | R (%) | 12.7 | 13.6 |
| Yield point | S (MPa) | 22.2 | 30 |
| Elongation at yield | S (%) | 2.5 | 3.1 |
| 3.5% bending stress | b3.5 (MPa) | 42.8 | 59 |
| Impact resistance | $a_n$ (kJ/m$^2$) | 24.3 | 46 |
| Modulus of elasticity in tension | (MPa) | 1630 | 1850 |

What is claimed is:

1. A chlorocarbonic ester of the formula

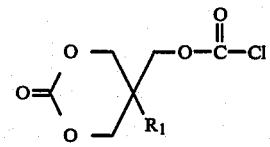

wherein $R_1$ represents an alkyl radical having 1 to 4 carbon atoms.

2. A chlorocarbonic ester according to claim 1 wherein $R_1$ represents methyl or ethyl.

3. A chlorocarbonic ester according to claim 1 wherein $R_1$ represents ethyl.

4. A polycyclic carbonic ester of the formula

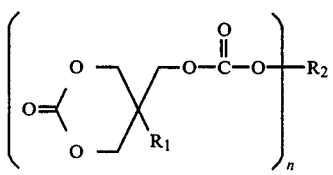

wherein

R₁ represents an alkyl radical having 1 to 4 carbon atoms,

R₂ represents alkylidene radical having 3 to 18 carbon atoms, an arylene radical having 6 to 12 carbon atoms or an aralkylene radical having 7 to 24 carbon atoms, and n denotes 2, 3 or 4.

5. A polycyclic carbonic ester according to claim 4 wherein

R₁ represents methyl or ethyl,

R₂ represents the hydrocarbon skeleton of an alcohol selected from the group consisting of trimethylolethane, trimethylolpropane, pentaerythritol, 1,4-butanediol, 2-butene-1,4-diol, 2-butyne-1,4-diol, neopentylglycol, 1,6-hexanediol, 2-methylene,-1,3-propanediol, 1,4-cyclohexanediol, cyclohexane-1,4-dimethanol, bisphenol A and perhydrobisphenol A, and n denotes the number of hydroxyl groups in the alcohol whose hydrocarbon skeleton is represented by R₂.

6. A polycyclic carbonic ester according to claim 4 wherein

R₂ has the formula

7. A polycyclic carbonic ester according to claim 4 wherein

R₂ has the formula

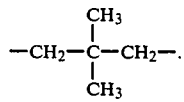

8. A polycyclic carbonic ester according to claim 4 wherein

R₂ has the formula

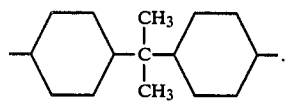

9. A polycyclic carbonic ester according to claim 4 wherein

R₂ has the formula

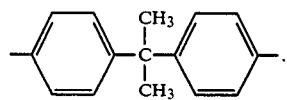

10. A polycyclic carbonic ester according to claim 4 wherein n=2.

* * * * *